United States Patent [19]
Patel

[11] 3,943,929
[45] Mar. 16, 1976

[54] MULTI-CHAMBER CONTAINER AND METHOD

[75] Inventor: Bhupendra C. Patel, Elgin, Ill.

[73] Assignee: The Kendall Company, Walpole, Mass.

[22] Filed: Nov. 15, 1974

[21] Appl. No.: 524,022

[52] U.S. Cl......... 128/275; 128/349 R; 128/DIG. 24
[51] Int. Cl.² ................... A61F 5/44; A61M 25/00
[58] Field of Search..... 128/2 F, 349, 348, DIG. 24, 128/295, 348, 275

[56] References Cited
UNITED STATES PATENTS

| | | | |
|---|---|---|---|
| 617,016 | 1/1899 | Harris | 128/349 R |
| 2,212,334 | 8/1940 | Wallerich | 128/349 R |
| 3,187,750 | 6/1965 | Tenczar | 128/DIG. 24 |
| 3,601,119 | 8/1971 | Engelsher | 128/2 F |
| 3,650,272 | 3/1972 | Ericson | 128/275 |
| 3,722,502 | 3/1973 | Besuner et al. | 128/2 F |
| 3,831,453 | 8/1974 | McWhorter | 128/2 F |

*Primary Examiner*—Lawrence W. Trapp
*Attorney, Agent, or Firm*—Powell L. Sprunger

[57] ABSTRACT

A multi-chamber container comprising a plurality of liquid drainage tubes, a receptacle having a plurality of separate liquid collection compartments, and means for separately connecting each of the drainage tubes to one of the separate compartments in order that liquid passes from the drainage tubes to the compartments for retention therein.

19 Claims, 6 Drawing Figures

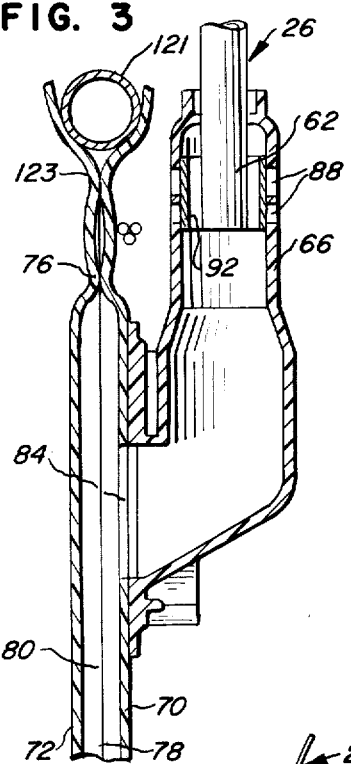
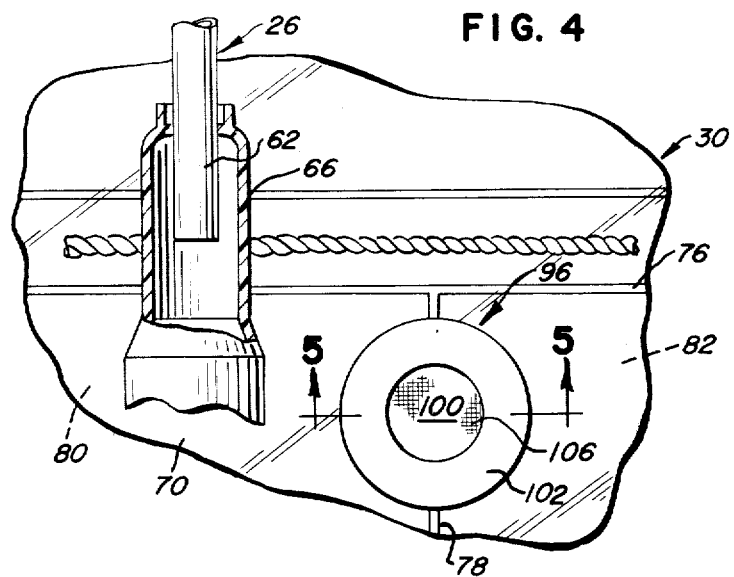
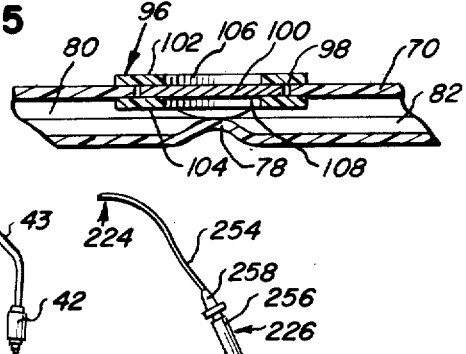
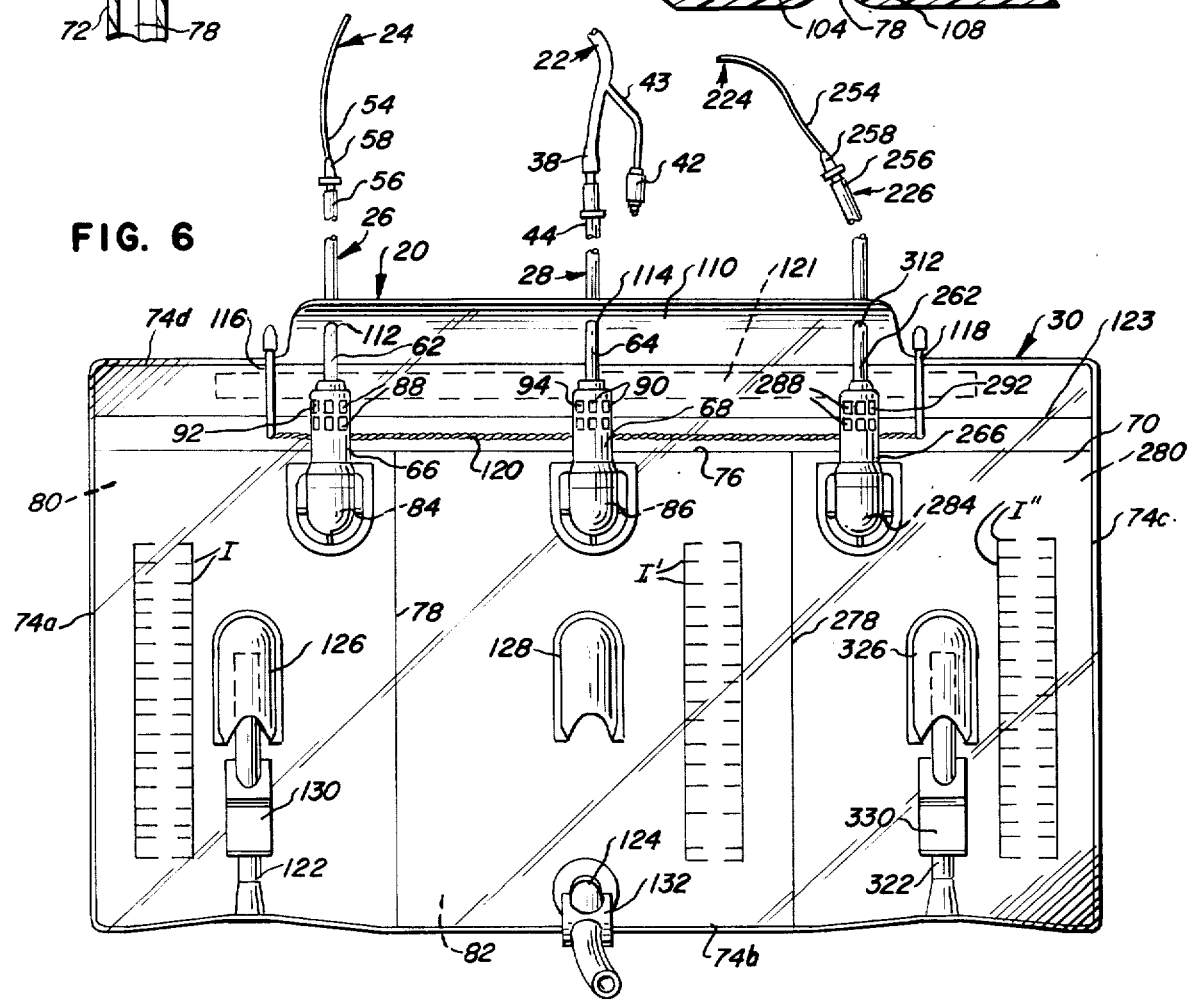

MULTI-CHAMBER CONTAINER AND METHOD

BACKGROUND OF THE INVENTION

The present invention relates to liquid drainage systems, amd more particularly to liquid collection receptacles.

In the past, catheters have been used to drain urine from a patient's bladder. In such a procedure, a distal end of the catheter, such as a Foley catheter, is inserted through the patient's urethra into the bladder, and a retention balloon adjacent the distal end of the catheter is inflated in the bladder to retain the catheter in place. The catheter has a drainage eye adjacent the distal end of the catheter communicating with a drainage lumen extending from the drainage eye to a proximal end of the catheter which remains outside the patient's body during use of the catheter. Accordingly, urine drains from the bladder through the drainage eye and lumen to the proximal end of the catheter after which the urine is collected in a receptacle.

On occasion it is necessary to drain urine directly from one or both of the patient's ureters or kidneys. For example, subsequent to certain ureterotomy procedures a ureteral catheter is passed through the urethra, bladder, and ureterovesicle junction, such that drainage eyes in the ureteral catheter are located upstream from the surgical site, and possibly in the enlarged renal pelvis adjacent the kidney. Urine drains through the drainage eyes and a drainage lumen extending through the ureteral catheter to a proximal end of the catheter outside the patient's body for collection of the urine. Thus, contact of a substantial amount of urine against the surgical site in the ureter is prevented. The Foley catheter is simultaneously used to drain urine passing from the uncatheterized ureter into the bladder and to drain any residual urine from the catheterized ureter which might eventually leak between the catheter and the ureter.

In the event that surgery has been performed on both ureters a second ureteral catheter is placed in the other ureter, and urine drains through both ureteral catheters, while residual urine is drained from the bladder through the Foley catheter, which may also be utilized to stabilize the ureteral catheters. A pair of ureteral catheters may also be used after surgery on the bladder to prevent urine from passing into the bladder. Similiarly, ureteral catheters may be used for both ureters during a partial differential study, where the relative output of urine from both kidneys is determined.

SUMMARY OF THE INVENTION

A principal feature of the present invention is the provision of a multi-chamber container of simplified construction for collecting urine from a plurality of catheters in a convenient and simplified manner.

The container comprises, a plurality of liquid drainage tubes separately communicating with the catheters, a receptacle having a plurality of separate liquid collection compartments, and means for separately connecting each of the drainage tubes to one of the separate compartments.

Thus, a feature of the present invention is that urine drains through the catheters and drainage tubes to separate compartments for collection therein.

Another feature of the invention is that the relative amount of urine drained through each of the catheters may be readily determined by the amount of urine collected in the compartments.

Yet another feature of the invention is that the separately collected urine is retained for separate diagnosis.

Still another feature of the invention is that each of the drainage tubes may be connected to the compartments by separate drip chambers to prevent retrograde bacterial movement from the compartments to the catheters.

A feature of the invention is that each of the compartments may be separately vented.

Yet another feature of the invention is that in one embodiment the compartments may be commonly vented.

Another feature of the invention is the provision of a method for catheterizing a patient with the container of the present invention.

Further features will become more fully apparent in the following description of the embodiments of this invention and from the appended claims.

DESCRIPTION OF THE DRAWINGS

In the drawings:

FIG. 3 is a fragmentary sectional veiw taken substantially as indicated along the line 3—3 of FIG. 1;

FIG. 4 is a fragmentary plan view, taken partly in section, of alternate venting means for the container of FIG. 1;

FIG. 5 is a fragmentary sectional view taken substantially as indicated along the line 5—5 of FIG. 4; and FIG. 6 is a fragmentary plan view of another embodiment of a multi-chamber container and liquid drainage system of the present invention.

DESCRIPTION OF THE PREFERRED EMBODIMENTS

Figure 1:
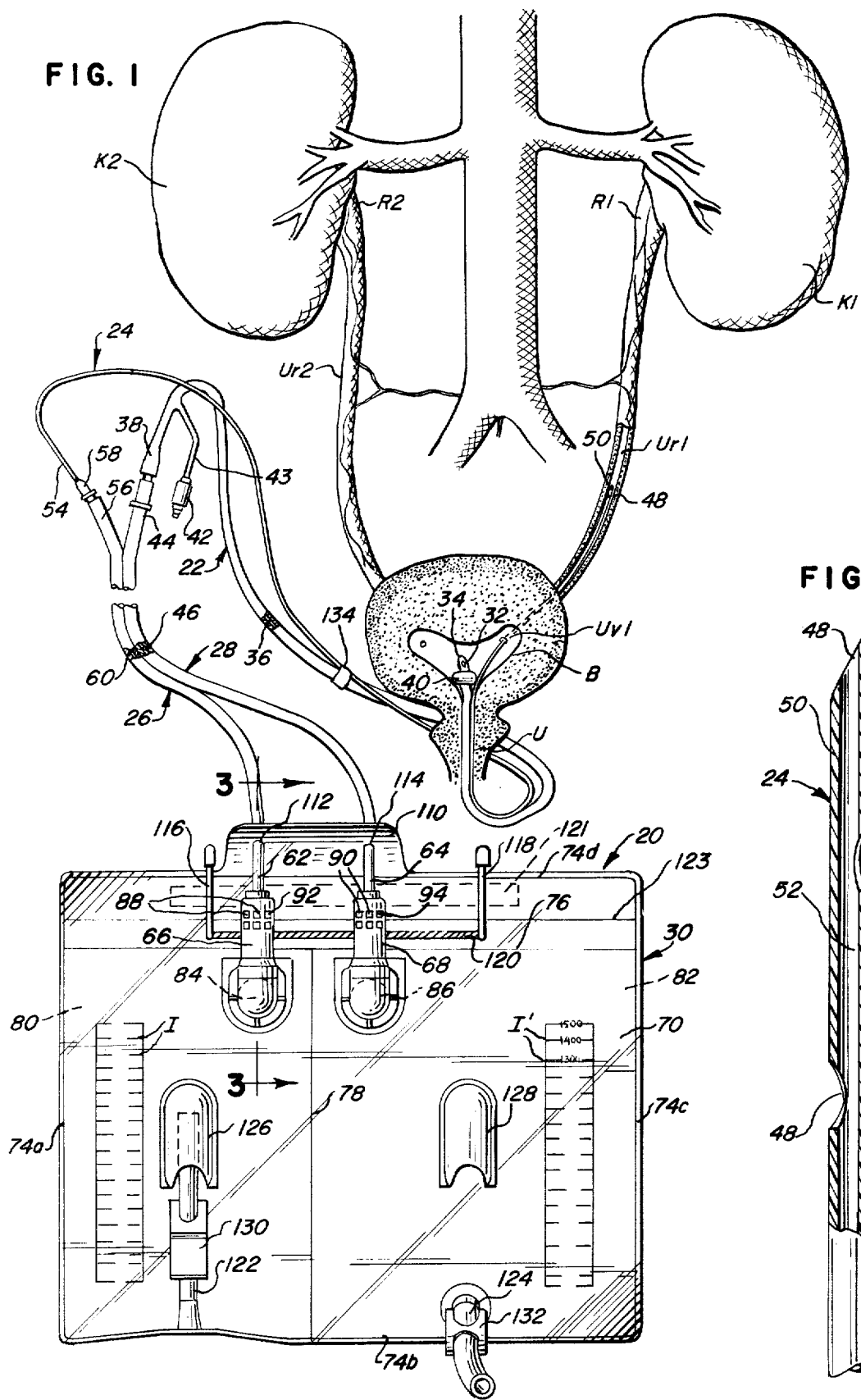
FIG. 1 is a fragmentary plan view, taken partly in section, of one embodiment of a multi-chamber container and liquid drainage system of the present invention.

Referring now to FIG. 1, there is shown a liquid drainage system generally designated 20 having a Foley or urinary catheter 22, a ureteral catheter 24, a pair of drainage tubes 26 and 28, and a container or receptacle 30. The Foley catheter 22 has a drainage eye 32 adjacent a distal end 34 of the catheter, and a drainage lumen 36 extending from the drainage eye 32 to a proximal end 38 of the catheter. The catheter 22 has an inflatable retention balloon 40 adjacent the distal end 34 of the catheter which is inflated through valve means 42 on a side arm 43 of the catheter and through an inflation lumen (not shown). The proximal end 38 of the catheter 22 is connected to an upstream end 44 of the drainage tube 28 with the drainage lumen 36 of the catheter 22 in communication with a drainage lumen 46 in the drainage tube 28.

Figure 2:
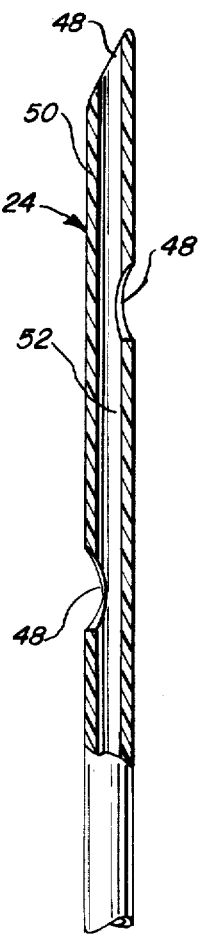
FIG. 2 is a fragmentary view on an enlarged scale, taken partly in section, of a ureteral catheter in the liquid drainage system of FIG. 1.

As shown in FIGS. 1 and 2, the ureteral catheter 24 has a plurality of drainage eyes 48 adjacent a distal end 50 of the catheter and a drainage lumen 52 extending from the drainage eyes 48 to a proximal end 54 of the catheter. The proximal end 54 of the catheter 24 is connected to an upstream end 56 of the drainage tube 26 by a connector 58 with the drainage lumen 52 in the catheter 24 in communication with a drainage lumen 60 in the drainage tube 26. As shown in FIGS. 1 and 3, downstream ends 62 and 64 of the drainage tubes 26 and 28, respectively, are received in and connected to a pair of connectors 66 and 68, preferably drip chambers, with the downstream ends 62 and 64 of the tubes 26 and 28 being spaced from the walls of the drip chambers to prevent retrograde bacterial movement through the drip chambers to the drainage tubes.

The receptacle or drainage bag 30 has a pair of flexible side walls 70 and 72, such as a plastic material, which are joined together along lines 74a, 74b, 74c, and 74d adjacent side edges of the bag. The side walls 70 and 72 are also joined together along a line 76 extending between the lines 74a and 74c toward the upper end of the bag, and a line 78 extending between the lines 74b and 76 intermediate the lines 74a and c, thus defining a pair of side-by-side separate compartments 80 and 82 in the bag. The side walls 70 and 72 may be joined together along the lines by any suitable means, such as by heat or radio frequency sealing. Preferably, the front wall 70 of the receptacle or bag 30 is transparent, and the side wall has vertically scaled indicia I and I' to indicate the volumes of urine separably collected in the compartments 80 and 82, respectively.

The side wall 70 has a pair of openings 84 and 86 communicating with and adjacent the upper end of each of the compartments 80 and 82. The drip chambers 66 and 68 are secured to the outer surface of the side wall 70 with the drip chambers in communication with the openings 84 and 86. Each of the drip chambers 66 and 68 has a plurality of openings 88 and 90 adjacent the upper end of the drip chambers, respectively, with the openings 88 and 90 being covered by air permeable filters 92 and 94, respectively, which permit passage of air into the drip chambers 66 and 68 while filtering bacteria from the air. Thus, in this embodiment of the container each of the compartments 80 and 82 are vented by a separate venting means in the drip chambers 66 and 68.

Alternatively, the compartments 80 and 82 may be vented through a single vent 96, as shown in FIGS. 4 and 5. In this embodiment, the side wall 70 has an opening 98 communicating with both of the compartments 80 and 82 adjacent the seal line 78, with an air permeable filter 100 being located in and substantially covering the opening 98. The vent 96 has a pair of flexible rings 102 and 104 secured to inner and outer surfaces of the wall 70 and retaining the filter 100 intermediate the rings in the opening 98. Thus, air passes through an opening 106 in the ring 102, the filter 100, and an opening 108 in the ring 104 to commonly vent the compartments 80 and 82.

As shown in FIG. 1, the bag 30 has a flexible flap 110 adjacent an upper end of the bag, and the flap 110 has a pair of openings 112 and 114 through which the drainage tubes 26 and 28 are threaded. The flap 110 serves to retain and stabilize the drainage tubes 26 and 28 in proper position above the bag. The bag 30 also may have a pair of clips 116 and 118 and a cord 120 for releasably attaching the bag 30 to a suitable fixture, such as a bed rail (not shown), during use of the drainage system. As illustrated in FIGS. 1 and 3, the bag 30 has an elongated tube 121 received intermediate the seal line 74d and a seal line 123 which extends between the seal lines 74a and c. The tube 121 stabilizes the upper end of the flexible bag 30 and prevents tearing out of the clips 116 and 118 from the bag during use.

As shown in FIG. 1, the receptacle 30 also has a pair of drain tubes 122 and 124 communicating with a lower end of the compartments 80 and 82, respectively. Outer ends of the drain tubes 122 and 124 may be moved from a first storage position, with the outer end of the tubes being located in pouches 126 and 128 secured to the outer surface of the side wall 70, as shown in connection with the compartment 80 in the drawing, and a second drainage position with the outer ends of the drain tubes being lowered, as shown in connection with the compartment 82 in the drawing. A pair of clips 130 and 132 releasably close the drain tubes 122 and 124, respectively, and may be opened when the drain tubes are in their second position to separately drain urine from the compartments.

In operation of the drainage system, the physician uses a cystoscope to locate ureteroversicle junction $Uv_1$ leading from the bladder B to the ureter $Ur_1$, after which he threads the ureteral catheter 24 through the urethra U, and the bladder B into the ureter $Ur_1$ with the drainage eyes 48 located in the ureter $Ur_1$. The physician then removes the cystoscope over the ureteral catheter 24. Next, the physician passes the distal end 34 of the Foley catheter 22 through the urethra U into the bladder B, after which the retention balloon 40 is inflated in the bladder B through the valve means 42 in the side arm 43 of the catheter by suitable means, such as a syringe (not shown). The inflated balloon 40 retains the catheter 22 in place, and also engages against the ureteral catheter 24 to assist in retaining the ureteral catheter at its proper location in the ureter. The ureteral catheter 24 may be secured to the Foley catheter 22 outside the patient's body by suitable means, such as a tape strip 134, to retain the ureteral catheter to the Foley catheter. Thus, if tension is applied to the proximal end 54 of the ureteral catheter 24, the tension is transmitted by the tape strip 134 to the Foley catheter 22, and the retention balloon 40 prevents dislodgment of the ureteral catheter from the ureter $Ur_1$. The proximal end 54 of the ureteral catheter 24 is connected to the upstream end 56 of the drainage tube 26 by the connector 58, while the proximal end 38 of the Foley catheter 22 is connected to the upstream end 44 of the drainage tube 28.

Thus, urine passing from the Kidney K1 through the ureter $Ur_1$ passes through the drainage eyes 48 of the ureteral catheter 24, through the drainage lumen 52 of the ureteral catheter, the drainage lumen 60 of the drainage tube 26, and the drip chamber 66 into the compartment 80 for collection. Similarly, urine passing from the kidney K2 passes through the ureter $Ur_2$ into the bladder B, through the drainage eye 32 and drainage lumen 36 of the Foley catheter 22, the drainage lumen 46 of the drainage tube 28, and the drip chamber 68 into the compartment 82 for collection. Residual urine which may eventually leak around the ureteral catheter 24 into the bladder B similarly drains into the compartment 82. Accordingly, urine from the ureter $Ur_1$ and bladder B are separately collected in an aseptic manner in the compartments 80 and 82. The relative quantity of the separately drained urine may be readily checked by viewing the volume of collected urine through the transparent side wall 70, or the relative volume of urine collected in the separate compartments may be determined by the indicia I and I' on the side wall 70. Separate samples of the collected urine may also be obtained for diagnosis through use of the drain tubes 122 and 124. It is noted that in certain procedures the distal end 50 of the ureteral catheter 24 may be inserted into the renal pelvis R1 adjacent the kidney K1.

Another embodiment of the liquid drainage system 20 of the present invention is illustrated in FIG. 6, in which like reference numerals designate like parts, and which will be described in connection with the anatomical diagram shown in FIG. 1. In this embodiment, the drainage system 20 has a second ureteral catheter 224, a second connector 258 connecting a downstream end 254 of the ureteral catheter 224 to an upstream end 256 of a third drainage tube 226, with a downstream end 262 of the drainage tube 226 being connected to a third connector or drip chamber 266. The drainage bag or receptacle 30 has a sealing line 278 extending between the lines 76 and 74b, with the seal lines 278, 76, 74b and 74c defining a third compartment 280. The drip chamber 266 is secured to the side wall 70 and communicates with the compartment 280 through an opening 284 in the side wall 70. The drainage tube 226 is retained in its proper position above the bag by an opening 312 extending through the flap 110. The drip chamber has a plurality of openings 288 adjacent an upper end of the drip chamber which is covered by an air permeable filter 292 to vent the drip chamber and compartment 280. The bag 30 has a drain tube 322 communicating with a lower end of the compartment 280 and having an outer end removably positioned in a pouch 326 secured to an outer surface of the side wall 70. The drain tube 322 is releasably closed by a clamp 330, and is movable between first and second positions, as previously described. The bag 30 also has a plurality of vertically spaced indicia I'' on the side wall 70 for determining the volume of urine collected in the third compartment 280.

The second ureteral catheter 224 associated with the third compartment 280 of the bag 30 operates similar to the first ureteral catheter 24 in draining urine. In this case, the second ureteral catheter 224 is threaded through the urethra U, the bladder B, and into the other ureter $Ur_2$, such that the drainage eyes of the second ureteral catheter 224 are located in ther ureter $Ur_2$ or the renal pelvis R2. Accordingly, urine drains through the drainage eyes and drainage lumen of the second ureteral catheter 224, through the connector 258 and the drainage lumen of the third drainage tube 226, and the third drip chamber 266 into the third compartment 280 for collection. Accordingly, urine from one kidney K1 drains into the first compartment 80, urine from the other kidney K2 drains into the third compartment 280, and residual urine drains from the bladder B into the second compartment 82, with the Foley catheter also being utilized to stabilize the ureteral catheters, as previously described. Thus, during a partial differential study the relative quantities of urine drained from the kidneys K1 and K2 may be readily determined by viewing the urine collected in the compartments 80 and 280, or by the indicia I or I'' associated with the compartments 80 and 280.

the foregoing detailed description is given for clearness of understanding only, and no unnecessary limitations should be understood therefrom, as modifications will be obvious to those skilled in the art. For example, it is apparent that the liquid drainage system described in connection with FIG. 1 may utilize a pair of ureteral catheters to drain urine from the ureters $Ur_1$ and $Ur_2$, without draining urine from the bladder B, if desired.

I claim:

1. A multi-chamber container for collecting urine from different sources, comprising:

a plurality of urine drainage tubes communicating with separate urine sources;

a receptacle having a plurality of separate urine collection compartments; and means for separately connecting each of said drainage tubes to one of said separate compartments for simultaneous passage of urine from the drainage tubes to the compartments and retention therein, said connecting means comprising a plurality of drip chambers connecting each of said drainage tubes to a separate compartment to prevent retrograde bacterial movement from said compartments.

2. The container of claim 1 wherein each of said drip chambers includes vent means for venting each of the drip chambers and compartments.

3. The container of claim 2 where in the vent means comprises opening means in each of the drip chambers and air-permeable filter means covering the opening means.

4. The container of claim 1 including means for separately venting each of said compartments.

5. The container of claim 1 wherein said container comprises a pair of flexible side walls joined together along spaced lines to define each of said compartments.

6. The container of claim 1 including means for commonly venting at least two of said compartments.

7. The container of claim 1 including means for draining each of said compartments.

8. The container of claim 1 wherein said receptacle includes flap means having opening means to receive and support each of said drainage tubes.

9. The container of claim 1 wherein said container has a pair of drainage tubes, and said receptacle has a pair of compartments.

10. The container of claim 1 wherein said container has three drainage tubes, and said receptacle has three compartments.

11. A multi-chamber container for collecting urine from different sources, comprising:

a plurality of urine drainage tubes communicating with separate urine sources;

a drainage bag having a pair of flexible side walls, means joining said side walls together along lines and defining a plurality of contiguous separate compartments, and a plurality of openings adjacent the upper ends of said compartments extending through a side wall with each of said openings communicating with one of said compartments;

a plurality of connectors connecting a downstream end of each of said drainage tubes with one of said openings for simultaneous passage of urine from the drainage tubes to separate compartments and retention therein; and means for venting each of said compartments to the atmosphere.

12. The container of claim 11 wherein said connectors comprise drip chambers secured to an outer surface of said side wall around said openings, each of said drip chambers receiving the downstream end of one of said drainage tubes adjacent an upper end of the drip chambers, with the downstream end of the drainage tubes being spaced from the walls of the drip chambers.

13. The container of claim 11 wherein said receptacle has first and second side-by-side compartments, and said venting means comprises opening means extending through one of said side walls and communicating with said first and second compartments adjacent the juncture of said compartments, an air-permeable filter covering said opening means, and means for securing the filter to said one side wall.

14. The container of claim 13 wherein the securing means comprises a pair of flexible rings, one of said rings being secured to an outer surface of said one side wall, and the other of said rings being secured to an inner surface of said one side wall, with said filter being located intermediate said rings.

15. The container of claim 11 wherein the joining means comprises sealing lines in said side walls.

16. A liquid drainage system for drainage of urine from different sources in a patient, comprising:
   a flexible receptacle having first and second separate compartments;
   first and second urine drainage tubes having drainage lumens;
   means for connecting a downstream end of the first and second tubes to the receptacle with the drainage lumens in the drainage tubes separately communicating with the first and second compartments;
   a ureteral catheter having a drainage lumen, a drainage eye communicating with the drainage lumen adjacent an upstream end of the ureteral catheter for placement in the patient's ureter, and a downstream end connected to an upstream end of the first drainage tube with the drainage lumen of the ureteral catheter communicating with the drainage lumen of the first drainage tube; and
   a urinary catheter having a drainage lumen, a drainage eye communicating with the drainage lumen adjacent an upstream end of the urinary catheter for placement in the patient's bladder, a retention member adjacent the upstream end of the urinary catheter, and a downstream end connected to an upstream end of the second drainage tube with the drainage lumen of the urinary catheter in communication with the drainage lumen of the second drainage tube, whereby urine from the patient's ureter and bladder are simultaneously collected in said separate compartments.

17. The drainage system of claim 16 wherein the receptacle includes a third compartment, including a third drainage tube and means for connecting a downstream end of the third drainage tube to the receptacle with the drainage lumen of the third drainage tube in separate communication with the third compartment, and including a second ureteral catheter having a drainage lumen, a drainage eye communicating with the drainage lumen adjacent an upstream end of the second ureteral catheter, and a downstream end connected to the third drainage tube with the drainage lumen of the second ureteral catheter in communication with the drainage lumen of the third tube.

18. A method of catheterizing a patient, comprising the steps of:
   draining urine associated with one kidney through a ureteral catheter from a location remote the bladder to a first compartment of a common drainage receptacle; and
   simultaneously and separately draining urine from the bladder through a urinary catheter to a separate second compartment in said common drainage receptacle.

19. The method of claim 18 including the step of separately and simultaneously draining urine associated with the other kidney through a second ureteral catheter from a location remote the bladder to a third separate compartment in said common drainage receptacle.

* * * * *